United States Patent [19]

Takase et al.

[11] Patent Number: 5,502,252

[45] Date of Patent: Mar. 26, 1996

[54] PROCESS OF PRODUCING INTERMEDIATES FOR USE IN PRODUCTION OF ALKOXYIMINOACETAMIDES AND INTERMEDIATES TO BE USED THEREIN

[75] Inventors: Akira Takase, Otsu; Hiroyuki Kai, Yamatokoriyama; Kuniyoshi Nishida, Koka; Moriyasu Masui, Yokkaichi, all of Japan

[73] Assignee: Shionogi & Co., Ltd., Osaka, Japan

[21] Appl. No.: 339,254

[22] Filed: Nov. 10, 1994

Related U.S. Application Data

[62] Division of Ser. No. 953,884, Sep. 30, 1992, Pat. No. 5,387,714.

[30] Foreign Application Priority Data

Oct. 4, 1991 [JP] Japan .................... 3-257513

[51] Int. Cl.$^6$ .................... C07C 233/05; C07C 231/02
[52] U.S. Cl. .................... 564/169; 549/510; 549/551; 549/553; 562/843; 564/133; 564/142; 564/163; 564/164
[58] Field of Search .................... 564/163, 164, 564/169; 562/843; 524/142, 133; 549/510, 551, 553

[56] References Cited

U.S. PATENT DOCUMENTS 5,118,833  6/1992  Mori et al. .................... 560/51

FOREIGN PATENT DOCUMENTS

| 0253213 | 1/1988 | European Pat. Off. . |
| 398692 | 11/1990 | European Pat. Off. . |
| 1959898 | 6/1970 | Germany . |
| 63-30463 | 2/1988 | Japan . |
| 63-23852 | 2/1988 | Japan . |
| 2192883 | 1/1988 | United Kingdom . |

OTHER PUBLICATIONS

Lapkin et al., J. Org. Chem., USSR, 11(9), pp. 1844–1848.
Sartori et al., Tetrahedron Letters, vol. 28, No. 14, pp. 1533–1536, 1987.
Burchardt, et al., Arch. Pharm., 321, pp. 311–312, 1988.
Burchardt, et al., Arch. Pharm., 323, pp. 181–183, 1990.
Soai, et al., Chemistry Letters, pp. 341–344, 1987.
Neunhoeffer, et al., Liebigs Ann. Chem., 1992, pp. 1271–1274.

Primary Examiner—Shailendra Kumar
Attorney, Agent, or Firm—Wenderoth, Lind & Ponack

[57] ABSTRACT

There is disclosed a process of producing an α-ketamide as an intermediate for use in the production of various alkoxyiminoacetamide compounds which are useful as fungicides. Also disclosed is an intermediate to be used in this process.

1 Claim, No Drawings

PROCESS OF PRODUCING INTERMEDIATES FOR USE IN PRODUCTION OF ALKOXYIMINOACETAMIDES AND INTERMEDIATES TO BE USED THEREIN

This is a divisional application of Ser. No. 07/953,884, filed Sep. 30, 1992, now U.S. Pat. No. 5,387,714.

FIELD OF THE INVENTION

The present invention relates to a process of producing an α-ketamide as an intermediate for use in the production of various alkoxyiminoacetamide compounds which are useful as fungicide,s and it also relates to an intermediate to be used in this process.

BACKGROUND OF THE INVENTION

Certain kinds of alkoxyimino compounds have recently received increased attention because of their excellent fungicidal effects on various fungi which may cause rice blast, rice sheath blight, cucumber downy mildew and the like. Some of these compounds and their production processes have already been known in the art (e.g., JP-A 63-23852 and JP-A 63-30463).

The present inventors have already filed several patent applications on alkoxyiminoacetamides compound of the formula:

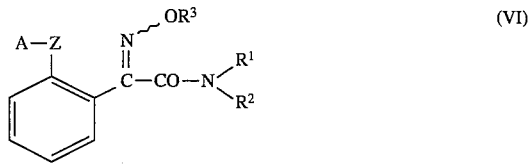

(VI)

wherein A is hydrogen, alkyl, alkenyl, alkynyl, alkoxy, halogenated alkyl, halogenated alkenyl, halogenated alkynyl, cycloalkyl, cycloalkenyl, unsubstituted or substituted phenyl, or an unsubstituted or substituted heterocyclic group; Z is —$CH_2$—, —O—, —S—, —CH(OH)—, —CO—, —NR— (wherein R is hydrogen or alkyl), —$CH_2CH_2$—, —CH=CH—, —$CH_2$O—, —$CH_2$S—, —$CH_2$S(O)—, —O$CH_2$—, —S(O)$CH_2$—, —S(O)$CH_2$— or epoxy; $R^1$ and $R^2$ are identically or differently hydrogen, alkyl or cycloalkyl; $R^3$ is alkyl or cycloalkyl; and the symbol "$\sim$" denotes a configuration of these compounds, i.e., either E- or Z-form, or a mixture of these forms, as well as on its production process (i.e., JP-A 2-127441, JP-A 2-200696 and JP-A 2-312519).

On the other hand, as disclosed in EP-A 398692, an α-ketamide of the formula:

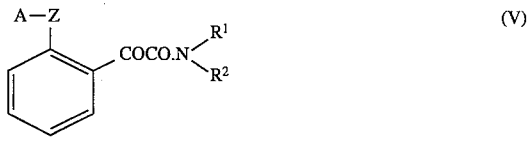

(V)

wherein A, Z, $R^1$ and $R^2$ are the same as described above, is important as a common intermediate for use in the production of various alkoxyiminoacetamide compounds of formula VI, and there is a great demand for the development of a process of producing such an α-ketamide with high efficiency.

OBJECTS OF THE INVENTION

Under these circumstances, the present inventors have paid much attention to the usefulness of an α-ketamide of formula V as a common intermediate and have intensively studied its production process. As the result, they have found that the α-ketamide can be obtained with high efficiency by reacting the corresponding halide with magnesium to form a Grignard reagent, reacting the obtained Grignard reagent with an oxalyl compound to form an α-keto acid halide, and reacting the obtained α-keto acid halide with an amine, thereby completing the present invention.

Thus, one object of the present invention is to provide a process of producing an α-ketamide with high efficiency, as a common intermediate for use in the production of various alkoxyiminoacetamide compounds which are useful as fungicides.

Another object of the present invention is to provide an α-keto acid halide as an intermediate to be used in the above process.

These objects as well as other objects and advantages of the present invention will become apparent to those skilled in the art from the following description.

SUMMARY OF THE INVENTION

According to the present invention, there is provided a process of producing an α-ketamide of the formula:

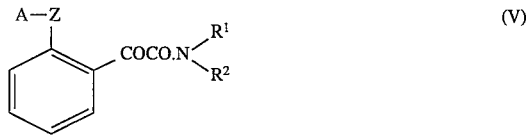

(V)

wherein A, Z, $R^1$ and $R^2$ are the same as described above, the process comprising the steps of reacting α-keto acid halide of the formula:

(III)

wherein A and Z are the same as described above and E is halogen, with an amine of the formula:

$HNR^1R^2$ (IV)

wherein $R^1$ and $R^2$ are the same as described above.

The α-keto acid halide of formula III can be obtained by reacting a halide of the formula:

(I)

wherein A and Z are the same as described above and X is halogen, with magnesium to form a Grignard reagent which is then reacted with an oxalyl compound of the formula:

$(COE)_2$ (II)

wherein E is the same as described above.

There is also provided an intermediate to be used in the above process, which comprises an α-keto acid halide of the formula:

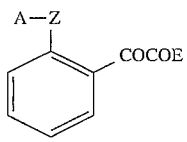 (III)

wherein A, Z and E are the same as described above.

particular, it is preferred that the halogen atom denoted by symbol E is chlorine. As used herein, the term "halogenated" refers to the substitution with at least one halogen atom selected from those described above.

The following will describe the procedures for the production of α-ketamide V.

For example, α-ketamide V can be produced through a route as shown in the reaction scheme:

REACTION SCHEME 1

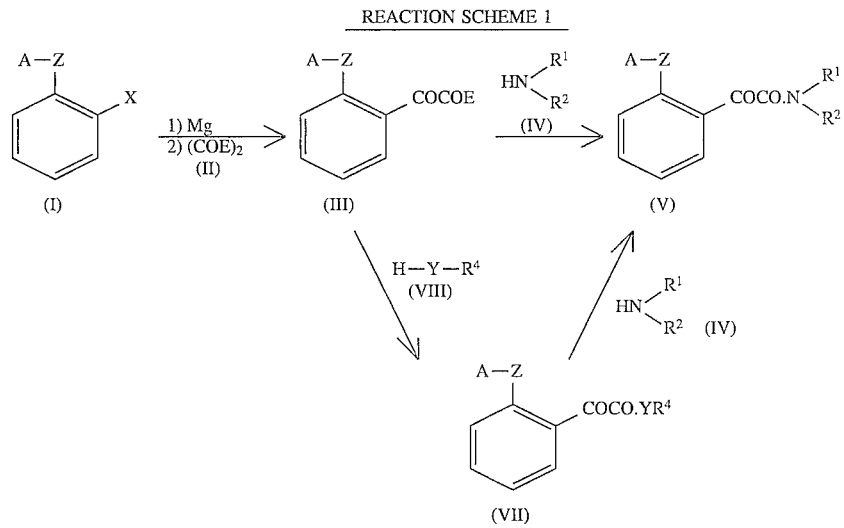

wherein Y is S or O, and the other symbols are the same as described above.

DETAILED DESCRIPTION OF THE INVENTION

In the above formulae, examples of the alkyl groups denoted by symbols A, R, $R^1$, $R^2$ and $R^3$ are $C_1$–$C_6$ alkyl, preferably $C_1$–$C_4$ alkyl such as methyl, ethyl, propyl, isopropyl, butyl, isobutyl and t-butyl. Examples of the alkenyl group denoted by symbol A are $C_2$–$C_6$ alkenyl, preferably $C_2$–$C_4$ alkenyl such as vinyl, allyl and crotyl. Examples of the alkynyl group denoted by symbol A are $C_2$–$C_6$ alkynyl, preferably $C_2$–$C_4$ alkynyl such as ethynyl, propargyl and butynyl. Examples of the alkoxy group denoted by symbol A are $C_1$–$C_6$ alkoxy, preferably $C_1$–$C_4$ alkoxy such as methoxy, ethoxy, propoxy and isopropoxy. Examples of the cycloalkyl groups denoted by symbols A, $R^1$, $R^2$ and $R^3$ are cyclopropyl, cyclopentyl and cyclohexyl. Examples of the cycloalkenyl group denoted by symbol A are cyclopentenyl and cyclohexenyl.

Also, examples of the heterocyclic group denoted by symbol A are pyridyl, pyrimidinyl, pyrazinyl, thiazolyl, benzothiazolyl, oxazolyl, benzoxazolyl, isoxazolyl, pyrazolyl, imidazolyl and quinolinyl. These heterocyclic groups and phenyl denoted by symbol A may be unsubstituted or substituted at any possible position on their ring with at least one substituent, preferably 1 to 3 substituents, selected from the group consisting of alkyl, alkenyl, alkynyl, alkoxy, halogenated alkyl, halogenated alkenyl, halogenated alkynyl, cycloalkyl, cycloalkenyl, unsubstituted or substituted phenyl, and unsubstituted or substituted heterocyclic groups.

Further, examples of the halogen atoms denoted by symbols E and X are fluorine, chlorine, bromine and iodine. In First, halide I is reacted in a solvent with magnesium at an amount of 1 to 4 equivalents, preferably 2 to 3 equivalents, per equivalent of halide I, thus obtaining a Grignard reagent. Examples of the solvent are ethers such as dry tetrahydrofuran (THF), diethyl ether and dibutyl ether. These solvents may be used solely or in combination with any other solvent, e.g., toluene or triethylamine. This reaction is conducted at a temperature in the range of room temperature to 150° C., preferably 40° to 70° C., for a period of 10 minutes to 48 hours, preferably 30 to 60 minutes. If necessary, any reaction activator such as iodine, dibromoethane or ethyl bromide may be used at an amount of 0.01 to 1.0 equivalent, preferably 0.05 to 0.2 equivalents, per equivalent of halide I.

For the conversion into compound III, the resulting Grignard reagent is dropwise added to a solution of oxalyl compound II in an appropriate solvent. The compound II is used at an amount of 1 to 3 equivalents, preferably 1 to 1.5 equivalents, per equivalent of the Grignard reagent. The dropwise addition is conducted at a temperature of −100° to 50° C., preferably −70° to 20° C. for a period of 1 to 60 minutes, preferably 10 to 30 minutes. Then, the reaction is allowed to proceed at a temperature of −100° to 50° C., preferably −75° to 20° C., for a period of 10 to 120 minutes, preferably 30 to 60 minutes. Examples of the solvent are inert solvents such as toluene, diethyl ether and THF. Examples of oxalyl compound II are oxalyl chloride and oxalyl bromide.

Alternatively, to the resulting Grignard reagent, oxalyl compound II may be dropwise added as such without dilution or as a solution in an appropriate solvent for the reaction. Examples of the solvent and the reaction conditions may be the same as described above. The α-keto acid halide III thus obtained may be isolated by a conventional technique or used for the subsequent steps without isolation and purification.

Next, as shown in the above reaction scheme 1, amine IV is dropwise added as such without dilution or as a solution in an appropriate solvent to compound III. In case where amine IV is in gas form, it is directly introduced into compound III. The dropwise addition or introduction is conducted at a temperature of −75° to 50° C., preferably −30° to 30° C. for a period of 1 to 60 minutes, preferably 5 to 10 minutes. The amine IV is used at an amount of 2.0 to 10 equivalents, preferably 2.0 to 4.0 equivalents, per equivalent of compound III. The reaction is allowed to proceed at a temperature of −20° to 70° C., preferably 0° to 30° C., for a period of 10 to 120 minutes, preferably 30 to 60 minutes, thus obtaining α-ketamide V.

Alternatively, as shown in the above reaction scheme 1, α-ketamide V may also be obtained by way of compound VII.

First, to the reaction mixture of α-keto acid halide III obtained as described above, anhydrous alcohol or anhydrous thiol VIII is added at a temperature of −75° to 50° C., preferably −30° to 30° C. Then, the reaction is allowed to proceed at a temperature of −50° to 70° C., preferably 0° to 30° C. for a period of 10 to 120 minutes, preferably 20 to 60 minutes, thus obtaining compound VII. The compound VIII is used at an amount of 1.0 to 10.0 equivalents, preferably 1.0 to 4.0 equivalents, per equivalent of compound III.

Then, compound VII is converted into compound V through its reaction with compound IV by dropwise addition of compound IV to compound VII. At that time, compound VII may be used without isolation from the reaction mixture, or may be used after isolation as a solution in an appropriate solvent such as THF, methanol or toluene. The amine IV is dropwise added thereto, as such without dilution or as a solution in an appropriate solvent. In case where amine IV is in gas form, it is directly introduced thereinto. The amine IV is used at an amount of 1.0 to 10.0 equivalents, preferably 1.0 to 4.0 equivalents, per equivalent of compound VII. The dropwise addition or introduction is conducted at a temperature of −20° to 70° C., preferably 0° to 30° C., for a period of 1 to 60 minutes, preferably 5 to 10 minutes. The reaction is allowed to proceed at a temperature of −20° to 70° C., preferably 0° to 30° C., for a period of 10 to 240 minutes, preferably 20 to 60 minutes, thus obtaining α-ketamide V.

The α-ketamide V obtained according to reaction scheme 1 is isolated as a crude product, and if necessary, purified by conventional isolation and purification techniques, after which it can be converted into alkoxyiminoacetamide compound VI through a route as shown in the following reaction scheme 2 or 3.

First, as shown in the reaction scheme:

REACTION SCHEME 2

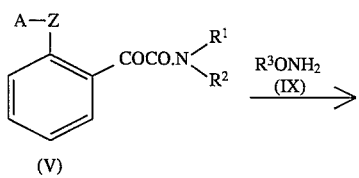

-continued
REACTION SCHEME 2

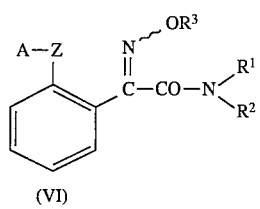

wherein all the symbols are the same as described above, compound VI can be obtained by reacting α-ketamide V with alkoxyamine IX for its conversion into an alkoxime.

Alternatively, as shown in the reaction scheme:

REACTION SCHEME 3

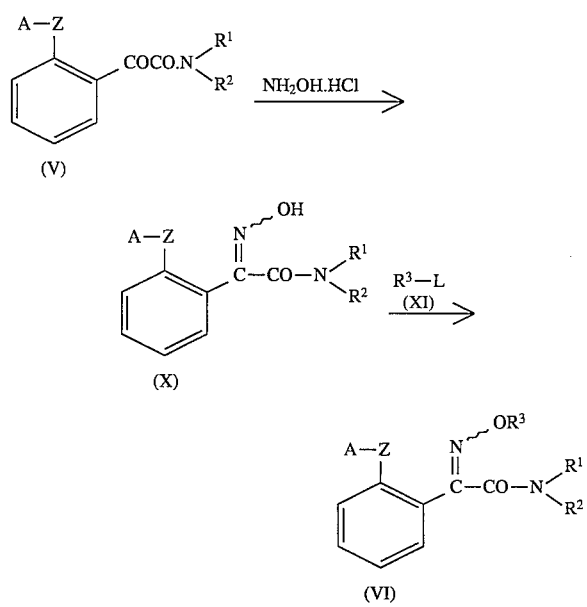

wherein L is halogen or $-OSO_2OR^3$, and the other symbols are the same as described above, compound VI can also be obtained by reacting α-ketamide V with hydroxylamine hydrochloride to form oxime X which is then reacted with alkylating agent XI for alkylation.

It has been found that the ratio of E-form to Z-form of oxime compound X or alkoximino compound VI, obtained from α-ketamide V as an intermediate, is greater than that of an oxime compound obtained by the conversion of α-keto ester (VII) thereinto as a conventional production route, i.e., E-form of the oxime compound which is more active can be obtained with higher yield in comparison with Z-form thereof.

The compound VI thus obtained can be further modified on its substituent, e.g., on the benzene ring, according to the reaction scheme:

REACTION SCHEME 4

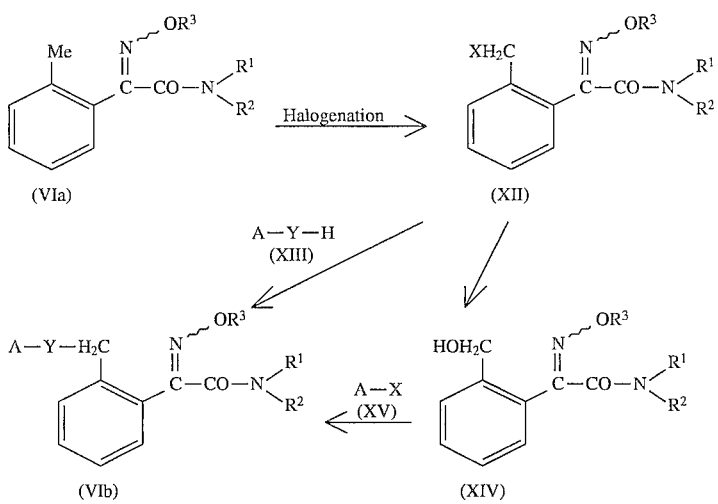

wherein all the symbols are the same as described above.

First, the methyl group on the benzene ring of compound VIa can be halogenated with a halogenating agent such as N-bromosuccinimide (NBS) and N-chlorosuccinimide (NCS) in the presence of α,α'-azobis(isobutyronitrile) to form a halogenated methyl group, thus obtaining compound XII. Then, the compound XII obtained can be reacted with alcohol or thiol XIII in the presence of a base to convert it into compound VIb. Examples of the base are potassium carbonate, sodium methoxide, sodium hydroxide and potassium hydroxide. Examples of compound XIII are substituted phenol, substituted thiophenol and hydroxy-substituted pyridine.

Further, the halogenated methyl group of compound XII can be reacted with potassium acetate and then subjected to hydrolysis, resulting in a hydroxymethyl group. The compound XIV obtained can be reacted with halide XV to convert it into ether compound VIb wherein Y is oxygen. Examples of halide XV are substituted chlorobenzene and halides of substituted heterocyclic compounds, such as substituted chloropyridine.

The alkoxyiminoacetamide compound VI thus obtained can be used as a fungicide in a conventional manner.

The present invention will be explained in more detail by way of the following Examples and Reference Examples, which are not to be construed to limit the scope thereof.

EXAMPLE 1

Production of N-methyl-2-[2-(biphenyl-4-yloxymethyl)phenyl]-2-oxoacetamide

In a stream of argon gas, 1-bromo-2-(biphenyl-4-yloxymethyl)benzene (33.92 g, 0.1 mol) in dry THF (140 ml) was dropwise added to a mixture of magnesium (4.86 g, 0.2 mol) and dibromoethane (0.2 ml) in dry THF (20 ml) at 50° to 60° C. over 40 minutes. The reaction mixture was stirred at 65° C. for 1 hour, diluted with dry THF (90 ml) and cooled below 20° C. This mixture was dropwise added to a solution of oxalyl chloride (15.23 g, 0.12 mol) in dry THF (250 ml) at −50° C. over 15 minutes, followed by stirring at −75° C. for 1 hour, and a 40% solution (46.59 g) of methylamine (0.6 mol) in methanol was added thereto at −20° C., followed by stirring at room temperature for 1 hour. After completion of the reaction, water (1000 ml) was added to the reaction mixture which was then adjusted to below pH 2 by addition of conc. HCl and extracted with ethyl acetate (600 ml). The extract was dried over anhydrous magnesium sulfate and concentrated under reduced pressure. The residue was purified by silica gel chromatography (ethyl acetate/n-hexane) to give N-methyl-2-[2-(biphenyl-4-yloxymethyl)phenyl]-2-oxoacetamide (24.52 g; yield, 71.0%) as colorless crystals.

m.p.: 144°–145° C. (ethyl acetate/n-hexane)

$^1$H-NMR (CDCl$_3$) δ ppm: 2.78 (d, 3H, J=5.9 Hz), 5.35 (s, 2H), 6.96–7.95 (m, 14H).

In the same manner as described above, were various compounds of formula V shown in Table 1.

TABLE 1

A—Z—[phenyl]—COCO.N(R$^1$)(R$^2$)  (V)

wherein R$^1$ is hydrogen, R$^2$ is methyl and the other symbols are as described below.

| A | Z | Yield (%) | m.p. (°C.) | $^1$H-NMR (CDCl$_3$) δ ppm |
|---|---|---|---|---|
| H | CH$_2$ | 64.1 | oil | 2.49(s, 3H), 2.98(d, 3H, J=5.9Hz), 7.06 (br, 1H), 7.26–7.95(m, 4H). |
| Ph* | O | 78.0 | 94–95 | 2.87(d, 3H, J=4.9Hz), 6.63(br, 1H), 6.86–7.78(m, 9H). |
| 2,5-Me$_2$Ph | OCH$_2$ | 69.9 | 129–130 | 2.16(s, 3H), 2.31(s, 3H), 2.80(d, 3H, J=4.9 Hz), 5.29(s, 2H), 6.69–7.99(m, 8H). |
| 3-BzlOPh | O | 49.3 | oil | 2.87(d, 3H, J=4.9Hz), 5.03(s, 2H), 6.64–7.78 (m, 13H). |

*: The compound I wherein X is chlorine was used as the starting material.

EXAMPLE 2

Production of N-methyl-2-(2-phenoxyphenyl)-2-oxoacetamide

In a stream of nitrogen gas, 2-chlorodiphenyl ether (10.23 g, 0.05 mol) in dry THF (20 ml) was dropwise added to a mixture of magnesium (1.34 g, 0.055 mol) and ethyl bromide (0.19 ml) in dry THF (15 ml) under reflux over 30 minutes. After further reflux for 6 hours, the reaction mixture was diluted with dry THF (15 ml) and cooled below 20° C. This mixture was dropwise added to oxalyl chloride (7.62 g, 0.06 mol) in dry THF (100 ml) at −10° to 0° C. over 15 minutes, followed by stirring at −10° to 0° C., and methylamine gas was introduced into the mixture, followed by stirring at room temperature for 15 minutes. After completion of the reaction, in 1N HCl (100 ml) was added to the reaction mixture which was then extracted with toluene (300 ml). The extract was washed with water and brine, dried over anhydrous magnesium sulfate and concentrated under reduced pressure. The residue was recrystallized from ethyl acetate/hexane to give N-methyl-2-(2-phenoxyphenyl)-2-oxoacetamide (8.07 g) as colorless crystals. The mother liquor was purified by silica gel chromatography (ethyl acetate/hexane) to give the objective compound (1.42 g). The total yield was 9.49 g (74%).

EXAMPLE 3

Production of 2-(2-methylphenyl)glyoxyloyl chloride

In a stream of argon gas, 2-bromotoluene (8.55 g, 0.05 mol) in dry THF (60 ml) was dropwise added to a mixture of magnesium (2.43 g, 0.1 mol) and dibromoethane (0.1 ml) in dry THF (10 ml) at 50° to 60° C. for 13 minutes. The reaction mixture was stirred at 60° to 65° C. for 1 hour, diluted with dry THF (30 ml) and cooled below 20° C. This mixture was dropwise added to oxalyl chloride (7.62 g, 0.06 mol) in dry ether (150 ml) below −50° C. over 8 minutes, followed by stirring at −75° C. for 1 hour, and filtered in a stream of argon gas at room temperature. The filtrate was concentrated under reduced pressure at room temperature. The precipitated crystals were filtered in a stream of argon gas and washed with dry ether. The filtrate and the wash liquid were combined together and the solvent was distilled off under reduced pressure to give crude 2-(2-methylphenyl)glyoxyloyl chloride (8.75 g; yield, 95.8%) as a pale brown oil.

IR $\nu_{max}$ (neat): 1795, 1696 cm$^{-1}$

In the same manner as described above, various compounds of formula III shown in Table 2 were produced.

TABLE 2

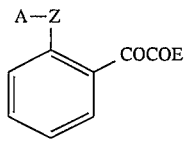

(III)

wherein E is chlorine and the other symbols are as described below.

| A | Z | Yield (%) | IR $\nu_{max}$ (neat) |
|---|---|---|---|
| Ph | O | 99.7 | 1780, 1680 |
| 2,5-Me$_2$Ph | OCH$_2$ | 99.0 | 1770, 1680 |

TABLE 2-continued (III)

wherein E is chlorine and the other symbols are as described below.

| A | Z | Yield (%) | IR $\nu_{max}$ (neat) |
|---|---|---|---|
| 4-Ph—Ph | OCH$_2$ | 99.8 | 1770, 1695 |

EXAMPLE 4

Production of N-methyl-2-(2-methylphenyl)-2-oxoacetamide

The crude 2-(2-methylphenyl)glyoxyloyl chloride (0.91 g, 5 mmol) were dissolved in dry THF (10 ml), and a 40% solution (1.55 g) of methylamine (20 mmol) in methanol was added thereto, followed by stirring at room temperature for 1 hour. After completion of the reaction, water (100 ml) was added to the reaction mixture which was then adjusted to below pH 2 by addition of conc. HCl and extracted with ethyl acetate (100 ml). The extract was dried over anhydrous magnesium sulfate and concentrated under reduced pressure. The residue was purified by silica gel chromatography (ethyl acetate/n-hexane) to give N-methyl- 2-(2-methylphenyl)-2-oxoacetamide (0.45 g; yield, 50.8%) as a colorless oil.

$^1$H-NMR (CDCl$_3$) δ ppm: 2.49 (s, 3H), 2.98 (d, 3H, J=5.9 Hz), 7.06 (br, 1H), 7.26–7.95 (m, 4H).

REFERENCE EXAMPLE 1

Production of N-methyl-2-(2-methylphenyl)-2-hydroxyiminoacetamide

To N-methyl-2-(2-methylphenyl)-2-oxoacetamide (5.31 g, 0.03 mol), added were methanol (30 ml) and hydroxylamine hydrochloride (4.17 g, 0.06 ml), and the reaction mixture was heated under reflux for 5 hours. After completion of the reaction, water (150 ml) was added to the reaction mixture which was then extracted with methylene chloride. The extract was dried over anhydrous magnesium sulfate and concentrated under reduced pressure. The residue was purified by silica gel chromatography (ethyl acetate/n-hexane) to give N-methyl-2-(2-methylphenyl)-2-hydroxyiminoacetamide in E-form (4.79 g; yield, 83.1%) and Z-form (0.50 g; yield, 8.7%) as colorless crystals.

E-form, m.p.: 160°–161° C. (ethyl acetate/n-hexane)
$^1$H-NMR (CDCl$_3$) δ ppm: 2.22 (s, 3H), 2.93 (d, 3H, J=4.9 Hz), 6.69 (br, 1H), 7.11–7.36 (m, 4H).

Z-form, m.p.: 166°–171° C. (ethyl acetate/n-hexane)
$^1$H-NMR (CDCl$_3$) δ ppm: 2.30 (s, 3H), 2.86 (d, 3H, J=4.9 Hz), 5.69 (br, 1H), 7.26–7.40 (m, 4H).

In the same manner as described above, various compounds of formula X shown in Table 3 were produced.

TABLE 3

$$\text{(X)}$$

Structure: A—Z attached to benzene ring with C(=N-OH)-CO-N(R¹)(R²) substituent wherein R¹ is hydrogen, R² is methyl
and the other symbols are described below.

| A | Z | Solvent | Yield (%) | m.p. (°C.) | ¹H-NMR (CDCl₃) δ ppm |
|---|---|---------|-----------|------------|-----------------------|
| 2,5-Me₂Ph | OCH₂ | EtOH | E 73.4 | 154–155.5 | 2.17(s, 3H), 2.29(s, 3H), 2.86(d, 3H, J=4.9Hz), 4.96(s, 2H), 6.64–7.61(m, 8H). |
|  |  |  | Z 26.0 | 139–141 | 2.15(s, 3H), 2.31(s, 3H), 2.77(d, 3H, J=4.9Hz), 5.06(s, 2H), 5.79(br, 1H), 6.69–7.68(m, 7H). |
| 4-Ph—Ph | OCH₂ | EtOH | E 73.4 | 162–163 | 2.90(d, 3H, J=4.9Hz), 5.03(s, 2H), 6.65(br, 1H), 6.95–7.58(m, 13H). |
|  |  |  | Z 25.5 | 173–179 | 2.81(d, 3H, J=4.9Hz), 5.13(s, 2H), 5.84(br, 1H), 6.95–7.63(m, 13H). |
| Ph | O | MeOH | E 97.8 | 183–184.5 | 2.84(d, 3H, J=4.9Hz), 6.77(br, 1H), 6.88–7.37(m, 9H). |

REFERENCE EXAMPLE 2

Production of
(E)-2-[2-(biphenyl-4-yloxymethyl)phenyl]
-2-methoxyimino-N-methylacetamide To (E)-2-[2-(biphenyl-4-yloxymethyl)phenyl]-2-hydroxyimino-N-methylacetamide (9.73 g, 0,027 mol), added were dry acetone (100 ml), potassium carbonate (11.20 g, 0.081 mol) and dimethylsulfate (6.81 g, 0.054 mol), and the reaction mixture was stirred overnight at room temperature. Then, undissolved materials were removed therefrom and the remaining mixture was concentrated under reduced pressure. The residue was purified by silica gel chromatography (ethyl acetate/n-hexane) to give (E)-2-[2-(biphenyl-4-yloxymethyl)-phenyl] -2-methoxyimino-N-methylacetamide (9.85 g; yield, 97.4%) as colorless crystals.

m.p.: 135.5°–137° C. (ethyl acetate/n-hexane)

¹H-NMR (CDCl₃) δ ppm: 2.90 (d, 3H, J=5.9 Hz), 3.94 (s, 3H), 4.99 (s, 2H), 6.71 (br, 1H), 6.94–7.55 (m, 13 H).

In the same manner as described above, various compounds of formula VI' shown in Table 4 were produced.

TABLE 4

$$\text{(VI')}$$

Structure: A—Z attached to benzene ring with C(=N-OR³)-CO-N(R¹)(R²) substituent wherein R¹ is hydrogen, R² and R³ are
both methyl and the other symbols are as described below.

| A | Z | Yield (%) | m.p. (°C.) | ¹H-NMR (CDCl₃) δ ppm |
|---|---|-----------|------------|-----------------------|
| H | CH₂ | 97.0 | 85.5–86.5 | 2.18(s, 3H), 2.93(d, 3H, J=5.9Hz), 3.96(s, 3H), 6.76(br, 1H), 7.08–7.29 (m, 4H). |
| 2,5-Me₂Ph | OCH₂ | 93.7 | 136–137 | 2.18(s, 3H), 2.29(s, 3H), 2.88(d, 3H, J=4.9Hz), 3.95(s, 3H), 4.92(s, 2H), 6.62–7.57(m, 8H). |
| Ph | O | 94.7 | 83–84 | 2.87(d, 3H, J=4.9Hz), 3.91(s, 3H), 6.63(br, 1H), 6.88–7.36(m, 9H). |

REFERENCE EXAMPLE 3

Production of
2-[2-(2,5-dimethylphenoxymethyl)-phenyl]
-2-methoxyimino-N-methylacetamide To 2-[2-(2,5-dimethylphenoxymethyl)phenyl]-N-methyl-2-oxoacetamide (0.27 g, 0.9 mmol), added were methanol (2.0 ml) and methoxylamine hydrochloride (0.15 g, 1.8 mmol), and the reaction mixture was heated under reflux for 4 hours. After completion of the reaction, water (100 ml) was added to the reaction mixture which was then extracted with methylene chloride. The extract was dried over anhydrous magnesium sulfate and concentrated under reduced pressure. The residue was purified by silica gel chromatography (ethyl acetate/n-hexane) to give 2-[2-(2,5-dimethylphenoxymethyl)phenyl] -2-methoxyimino-N-methylacetamide (0.28 g; yield, 98.9 %) as a mixture of E-form and Z-form.

¹H-NMR (CDCl₃) δ ppm: 2.18–2.30 (m, 6H), 2.84–2.89 (m, 3H), 3.95 (s, 1.5 H), 4.01 (s, 1.5 H), 4.92 (s, 1H), 5.17 (s, 1H), 6.62–7.59 (m, 8H).

REFERENCE EXAMPLE 4

Production of
(E)-2-(2-bromomethylphenyl)-2-methoxyimino-N-
methylacetamide

To (E)-2-methoxyimino-2-(2-methylphenyl)-N-methylacetamide (2.66 g, 0.01 mol), added were carbon tetrachloride (20 ml), NBS (1.96 g, 0.011 mol) and α,α'-azobis(isobutyronitrile) (0.16 g, 0.001 mol), and the reaction mixture was heated under reflux for 1 hour. After completion of the reaction, undissolved materials were removed and the remaining mixture was concentrated under reduced pressure. The residue was purified by silica gel chromatography (ethyl acetate/toluene) to give (E)-2-(2-bromomethylphenyl)- 2-methoxyimino-N-methylacetamide (1.08 g; yield, 37.7%) as an oil.

¹H-NMR (CDCl₃) δ ppm: 2.93 (d, 3H, J=4.9 Hz), 3.99 (s, 3H), 4.36 (s, 2H), 6.81 (br, 1H), 7.15–7.50 (m, 4H).

REFERENCE EXAMPLE 5

Production of
(E)-2-[2-(2,5-dimethylphenoxymethyl)-phenyl]
-2-methoxyimino-N-methylacetamide To (E)-2-(2-bromomethylphenyl)-2-methoxyimino-N-methylacetamide (0.72 g, 2.5 mmol), added were dry DMF (5.0 ml), 2,5-dimethylphenol (0.46 g, 3.75 mmol) and potassium carbonate (0.69 g, 5.0 mmol), and the reaction mixture was stirred at room temperature for 4 hours. Then, water (100 ml) was added to the reaction mixture which was then extracted with ethyl acetate (100 ml). The extract was washed with water (100 ml), dried over anhydrous magnesium sulfate and concentrated under reduced pressure. The residue was purified by silica gel chromatography (ethyl acetate/n-hexane) to give (E)-2-[2-(2,5-dimethylphenoxymethyl)phenyl] -2-methoxyimino-N-methylacetamide (0.57 g) as colorless crystals (yield, 69.8%).

REFERENCE EXAMPLE 6

Production of methyl
2-[2-(biphenyl-4-yloxymethyl)phenyl] -2-oxoacetate

In a stream of argon gas, 1-bromo-2-(biphenyl-4-yloxymethyl)benzene (16.96 g, 0.05 mol) in dry THF (70 ml) was dropwise added to a mixture of magnesium (2.43 g, 0.1 mol) and dibromoethane (0.1 ml) in dry THF (10 ml) at 50° to 60° C. over 20 minutes. The reaction mixture was stirred at 65° C. for 1 hour, diluted with dry THF (20 ml) and cooled below 20° C. The mixture was dropwise added to oxalyl chloride (7.61 g, 0.06 mol) in dry THF (150 ml) below −15° C. over 15 minutes, followed by stirring at −75° C. for 1 hour, and anhydrous methanol (12.82 g, 0.4 mol) was added thereto below −50° C., followed by stirring at room temperature for 1 hour. After completion of the reaction, aqueous ammonium chloride (500 ml) was added to the reaction mixture which was then extracted with ether (400 ml). The extract was dried over anhydrous magnesium sulfate and concentrated under reduced pressure. The residue was purified by silica gel chromatography (ethyl acetate/toluene) to give methyl 2-[2-(biphenyl-4-yloxymethyl)phenyl]-2-oxoacetate (11.79 g; yield, 68.1%) as pale yellow crystals.
m.p.: 106°–107° C.

¹H-NMR (CDCl₃) δ ppm: 3.86 (s, 3H), 5.45 (s, 2H), 7.03–7.83 (m, 13H).

REFERENCE EXAMPLE 7

Production of
N-methyl-2-[2-(biphenyl-4-yloxymethyl)phenyl]
-2-oxoacetamide

To methyl 2-[2-(biphenyl-4-yloxymethyl)phenyl]-2-oxoacetate (3.46 g, 0.01 mol), added were anhydrous methanol (10 ml), dry THF (10 ml) and a 40% solution (2.33 g) of methyl amine (0.03 mol) in methanol, and the reaction mixture was stirred at room temperature for 2 hour. After completion of the reaction, water (150 ml) was added to the reaction mixture which was then adjusted to below pH 2 by addition of conc. HCl and extracted with ethyl acetate (150 ml). The extract was dried over anhydrous magnesium sulfate and concentrated under reduced pressure. The obtained crystals (3.42 g; yield, 99.1%) were recrystallized from ethyl acetate/n-hexane to give N-methyl-2-[2-(biphenyl-4-yloxymethyl)phenyl] -2-oxoacetamide (2.83 g) as colorless crystals (m.p.: 144°–145° C.).

¹H-NMR (CDCl₃) δ ppm: 2.78 (d, 3H, J=5.9 Hz), 5.35 (s, 2H), 6.96–7.95 (m, 14H).

What is claimed is:

1. A process of producing an α-ketamide of the formula:

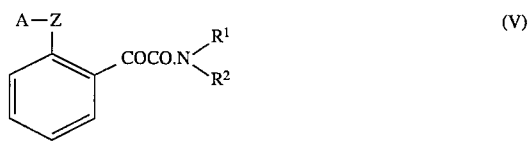

wherein A is alkyl, unsubstituted phenyl or phenyl substituted by at least one substituent selected from the group consisting of alkyl, alkenyl, alkynyl, alkoxy, halogenated alkyl, halogenated alkenyl, halogenated alkynyl, cycloalkyl, cycloalkenyl and unsubstituted phenyl groups; Z is —CH₂—, —O—, —S—, —CH(OH)—, —CO—, —NR— (wherein R is hydrogen or alkyl), —CH₂CH₂—, —CH=CH—, —CH₂O—, —CH₂S—, —CH₂S(O)—, —OCH₂—, —SCH₂—, —S(O)CH₂— or epoxy; and R¹ and R² are identically or differently hydrogen, alkyl or cycloalkyl, the process comprising the steps of:

reacting a halide of the formula:

wherein A and Z are the same as described above and X is halogen, with magnesium;

reacting the resultant reaction product with an oxalyl compound of the formula:

(COE)₂ (II)

wherein E is the same as described above, to form an α-keto acid halide of the formula:

wherein A and Z are the same as described above and E is halogen; and reacting the α-keto acid halide with an amine of the formula:
wherein R¹ and R² are the same as described above.

* * * * *